US00PP27818P2

(12) United States Plant Patent
Flore

(10) Patent No.: US PP27,818 P2
(45) Date of Patent: Mar. 28, 2017

(54) ***PHALAENOPSIS* PLANT NAMED 'MI00202'**

(50) Latin Name: *Phalaenopsis hybrida*
Varietal Denomination: MI00202

(71) Applicant: Febe Flore, Lochristi (BE)

(72) Inventor: Febe Flore, Lochristi (BE)

(73) Assignee: Floreac N.V. div. Microflor, Lochristi (BE)

( * ) Notice: Subject to any disclaimer, the term of this patent is extended or adjusted under 35 U.S.C. 154(b) by 0 days.

(21) Appl. No.: 14/756,929

(22) Filed: Oct. 30, 2015

(51) Int. Cl.
*A01H 5/02* (2006.01)

(52) U.S. Cl.
USPC ..... Plt./311

(58) Field of Classification Search
USPC ..... Plt./311
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Phalaenopsis* plant named 'MI00202', characterized by its upright plant habit; moderately vigorous growth habit; strong flowering stems; freely flowering habit; typically two panicles or racemes per plant; each inflorescence with numerous flowers; showy light purple-colored flowers with fine dots and lighter-colored centers; and ease of production.

2 Drawing Sheets

Botanical designation: *Phalaenopsis hybrida.*
Cultivar denomination: 'MI00202'.

BACKGROUND OF THE INVENTION

The present invention relates to a new and distinct cultivar of *Phalaenopsis* plant, botanically known as *Phalaenopsis hybrida*, and hereinafter referred to by the name 'MI00202'.

The new *Phalaenopsis* plant is a product of a planned breeding program conducted by the Inventor in Lochristi, Belgium. The objective of the breeding program is to develop new freely flowering *Phalaenopsis* plants with unique and attractive flower patterns and coloration.

The new *Phalaenopsis* plant originated from a cross-pollination in July, 2005 in Lochristi, Belgium of a proprietary selection of *Phalaenopsis hybrida* identified as code number PHM00405, not patented, as the female, or seed, parent with a proprietary selection of *Phalaenopsis hybrida* identified as code number PHM00058, not patented, as the male, or pollen, parent. The new *Phalaenopsis* plant was discovered and selected by the Inventor as a single flowering plant from within the progeny of the stated cross-pollination grown in a controlled greenhouse environment in Lochristi, Belgium in July, 2008.

Asexual reproduction of the new *Phalaenopsis* plant by in vitro propagation (tissue culture) in a controlled environment in Lochristi, Belgium since February, 2010 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'MI00202'. These characteristics in combination distinguish 'MI00202' as a new and distinct *Phalaenopsis* plant:

1. Upright plant habit.
2. Moderately vigorous growth habit.
3. Strong flowering stems.
4. Freely flowering habit; typically two panicles or racemes per plant; each inflorescence with numerous flowers.
5. Showy light purple-colored flowers with fine dots and lighter-colored centers.
6. Ease of production.

Plants of the new *Phalaenopsis* can be compared to plants of the female parent selection. Plants of the new *Phalaenopsis* differ primarily from plants of the female parent selection in flower color as flowers plants of the female parent selection have violet-colored labellums.

Plants of the new *Phalaenopsis* can be compared to plants of the male parent selection. Plants of the new *Phalaenopsis* differ primarily from plants of the male parent selection in flower color as plants of the male parent selection have flowers with violet-colored margins and heavily dotted centers.

Plants of the new *Phalaenopsis* can be compared to plants of *Phalaenopsis hybrida* 'SOGO F1582', disclosed in U.S. Plant Pat, No. 20,383. In side-by-side comparisons conducted in Lochristi, Belgium, plants of the new *Phalaenopsis* differ primarily from plants of 'SOGO F1582' in petal size as plants of the new *Phalaenopsis* have longer petals. Additionally, the central lobe of the labellum of plants of the new *Phalaenopsis* is hastate-deltoid in shape whereas the central lobe of the labellum of plants of 'SOGO F1582' is ovate in shape.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet is a side perspective view of a typical flowering plant of 'MI00202' grown in a container.

The photograph on the second sheet is a close-up view of typical flowers of 'MI00202'.

DETAILED BOTANICAL DESCRIPTION

The aforementioned photographs and following observations and measurements describe plants grown during the summer in 12-cm containers in a glass-covered greenhouse in Lochristi, Belgium and under cultural practices typically used in commercial *Phalaenopsis* production. During the production of the plants, day and night temperatures ranged from 18° C. to 29° C. and light levels ranged from 150 Watt/$m^2$ to 375 Watt/$m^2$. Plants were exposed to eight weeks of cooling to induce flowering. Plants were 76 weeks from propagation when the photographs and description were taken. In the following description, color references are made to The Royal Horticultural Society Colour Chart, 2015 Edition, except where general terms of ordinary dictionary significance are used.

Botanical classification: *Phalaenopsis hybrida* 'MI00202'.

Parentage:

*Female parent*.—Proprietary selection of *Phalaenopsis hybrida* identified as code number PHM00405, not patented.

*Male parent*.—Proprietary selection of *Phalaenopsis hybrida* identified as code number PHM00058, not patented.

Propagation:

*Type*.—By in vitro propagation (tissue culture).

*Time to initiate roots, summer*.—About nine to ten weeks at temperatures about 26° C.

*Time to initiate roots, winter*.—About ten to eleven weeks at temperatures about 26° C.

*Time to produce a rooted young plant, summer*.—About 140 to 160 weeks at temperatures about 26° C.

*Time to produce a rooted young plant, winter*.—About 150 to 180 weeks at temperatures about 26° C.

*Root description*.—Thick, fleshy; typically grey green in color, towards the apex, close to light green occasionally with a purple-colored blush.

*Rooting habit*.—Non-branching; sparse.

Plant description:

*Plant form and growth habit*.—Herbaceous epiphyte; upright plant habit with typically two panicles or racemes per plant, each inflorescence with numerous flowers; monopodial; moderately vigorous growth habit and moderate growth rate; easy to produce.

*Plant height, substrate level to top of foliar plane*.—About 11.5 cm.

*Plant height, substrate level to top of inflorescences*.—About 58.4 cm.

*Plant diameter or spread*.—About 43 cm.

Leaf description:

*Arrangement*.—Distichous, simple; sessile.

*Length*.—About 21.4 cm.

*Width*.—About 7.3 cm.

*Aspect*.—Arching.

*Shape*.—Oblong to obovate.

*Apex*.—Obtuse, unequal.

*Base*.—Sheathing.

*Margin*.—Entire; very slightly revolute.

*Texture, upper and lower surfaces*.—Slightly furrowed; glabrous; durable.

*Luster, upper and lower surfaces*.—Moderately glossy.

*Venation pattern*.—Camptodromous.

*Color*.—Developing and fully expanded leaves, upper surface: Close to between 143A and 146A; venation, close to between 143A and 146A. Developing and fully expanded leaves, lower surface: Close to between 143C and 147B; venation, close to 144B.

Inflorescence description:

*Appearance and flowering habit*.—Showy zygomorphic flowers arranged on axillary panicles or racemes; typically two racemes per plant; each inflorescence with about twelve flowers; flowers face outwardly on arching inflorescences supported by strong upright peduncles; flowers with three petals, one petal transformed into a labellum and three sepals.

*Fragrance*.—None detected.

*Time to flower*.—Plants begin flowering about 18 weeks after an inductive cooling period.

*Flower longevity*.—Individual flowers maintain good substance for about three months on the plant; flowers not persistent.

*Inflorescence length* (*lowermost flower to inflorescence apex*).—About 39.8 cm.

*Inflorescence width*.—About 17.8 cm to 43 cm.

*Flower buds*.—Height: About 8 mm. Diameter: About 7 mm. Shape: Ovoid. Color: Close to 200B to 200C.

*Flower diameter*.—About 10.5 cm.

*Flower depth*.—About 3.9 cm.

*Petals, quantity and arrangement*.—Three, two lateral petals and one lower petal transformed into a labellum.

*Lateral petals*.—Length: About 5.1 cm. Width: About 6.2 cm. Shape: Reniform. Apex: Rounded. Margin: Entire. Texture, upper and lower surfaces: Glabrous; moderately velvety. Luster, upper and lower surfaces: Matte. Color: When opening, upper surface: Close to 84D to lighter than 84D; very densely covered with fine dots, close to N78B; overall color impression, close to N78C. When opening, lower surface: Close to N78C; venation, close to N78B; center, close to between 76D and NN155D. Fully opened, upper surface: Close to 84D to lighter than 84D; very densely covered with fine dots, close to N78B; towards the margins, dots closer to N78C; main vein, close to N80A; towards the base, close to between 76D and NN155D; overall color impression, close to N78C; color does not fade with development. Fully opened, lower surface: Close to N78C; venation, close to N78B; center, close to between 76D and NN155D.

*Labellum*.—Length: About 3.3 cm. Width: About 2.9 cm. Shape: Tri-lobed; two lateral lobes, reniform; central lobe, hastate-deltoid. Apex: Lateral lobes, rounded; central lobe, cleft with two long narrow recurved tips. Callosities: Located at the base of the labellum and attachment point of the lateral petals; about 5 mm in length, about 6 mm in width and about 6 mm in height. Margin: Entire. Texture, upper and lower surfaces: Glabrous; slightly velvety. Luster, upper and lower surfaces: Matte. Color: When opening and fully opened, upper surface: Lateral lobes: Close to NN155D; towards the margins, tinged with close to 75B to 75C; towards the base, tinged, dotted and marbled with close to 59B to 59C and 16B. Central lobe: Close to NN155D; towards the margins, close to 64A to 64B with marbling, close to 22C; towards the apex, close to N78A and apices, close to 8D; towards the base, close to 16A to 16B; main vein, proximally, close to 60B. Callosities: Close to 17A; fine dots, close to 59A to 59B. When opening and fully opened, lower surface: Lateral lobes: Close to NN155D; distal half, close to 75B to 75C; towards the base, tinged, dotted and marbled with close to 60C and 16B. Central lobe: Close to between 77C to N78D; towards the base, close to N78B; margins, close to 71C and 187D and marbled with close to 22B; apices, close to 8D.

*Sepals, quantity and arrangement*.—Three, two lower lateral sepals and one upper dorsal sepal.

*Lateral sepals*.—Length: About 5.3 cm. Width: About 2.8 cm. Shape: Ovate. Apex: Acute. Base: Obtuse to truncate. Margin: Entire. Texture, upper and lower surfaces: Glabrous; moderately velvety. Luster, upper and lower surfaces: Matte. Color: When opening, upper surface: Close to 84D to lighter than 84D; very densely covered with fine dots, close to N78B; towards the base, larger dots and marbling, close to N78A; overall color impression, close to N78C. When opening, lower surface: Close to N78B and N78C; towards the base, close to 155B. Fully opened, upper surface: Close to 84D to lighter than 84D; very densely covered with fine dots, close to N78B; towards the base, larger dots and marbling, close to N78A; overall color impression, close to N78C; color does not fade with development. Fully opened, lower surface: Close to N78C; towards the base, close to 155C.

*Dorsal sepal*.—Length: About 5.2 cm. Width: About 3.3 cm. Shape: Ovate to nearly oblong. Apex: Broadly acute. Base: Obtuse to truncate. Margin: Entire. Texture, upper and lower surfaces: Glabrous; moderately velvety. Luster, upper and lower surfaces: Matte. Color: When opening and fully opened, upper surface: Close to 84D to lighter than 84D; very densely covered with fine dots, close to N78B; towards the apex, dots, close to N78C. When opening and fully opened, lower surface: Close to N78B to N78D; towards the base, venation, close to N78B.

*Peduncles*.—Length: About 71.7 cm. Diameter: About 5.5 mm. Strength: Very strong. Aspect: Upright to about 45° from vertical. Texture: Smooth, glabrous. Luster: Matte. Color: Close to 197A heavily dotted with close to 146C to 146D.

*Pedicels*.—Length: About 5 cm. Diameter: About 4 mm. Strength: Moderately strong. Aspect: About 60° from peduncle axis. Texture: Smooth, glabrous. Luster: Matte. Color: Close to 145C to 145D.

*Reproductive organs*.—Androecium: Column length: About 1 cm. Column width: About 6 mm. Column color: Close to NN155D; upper surface and apex, tinged with close to N78C and N78D. Pollinia quantity: Two. Pollinia diameter (per two pollinia): About 2 mm. Pollinia color: Close to 21A.

*Gynoecium*.—Stigma length: About 3 mm. Stigma width: About 5 mm. Stigma shape: Reniform to nearly orbicular. Stigma color: Close to NN155D. Ovary length: About 4.5 mm. Ovary diameter: About 4 mm. Ovary color: Close to 145C to 145D. Seeds and fruits: Seed and fruit development have not been observed on plants of the new *Phalaenopsis*.

Disease & pest resistance: Plants of the new *Phalaenopsis* have not been shown to be resistant to pathogens and pests common to *Phalaenopsis* plants.

Temperature tolerance: Plants of the new *Phalaenopsis* have been observed to tolerate high temperatures of about 40° C. and suitable for USDA Hardiness Zone 10.

It is claimed:

1. A new and distinct *Phalaenopsis* plant named 'MI00202' as illustrated and described.

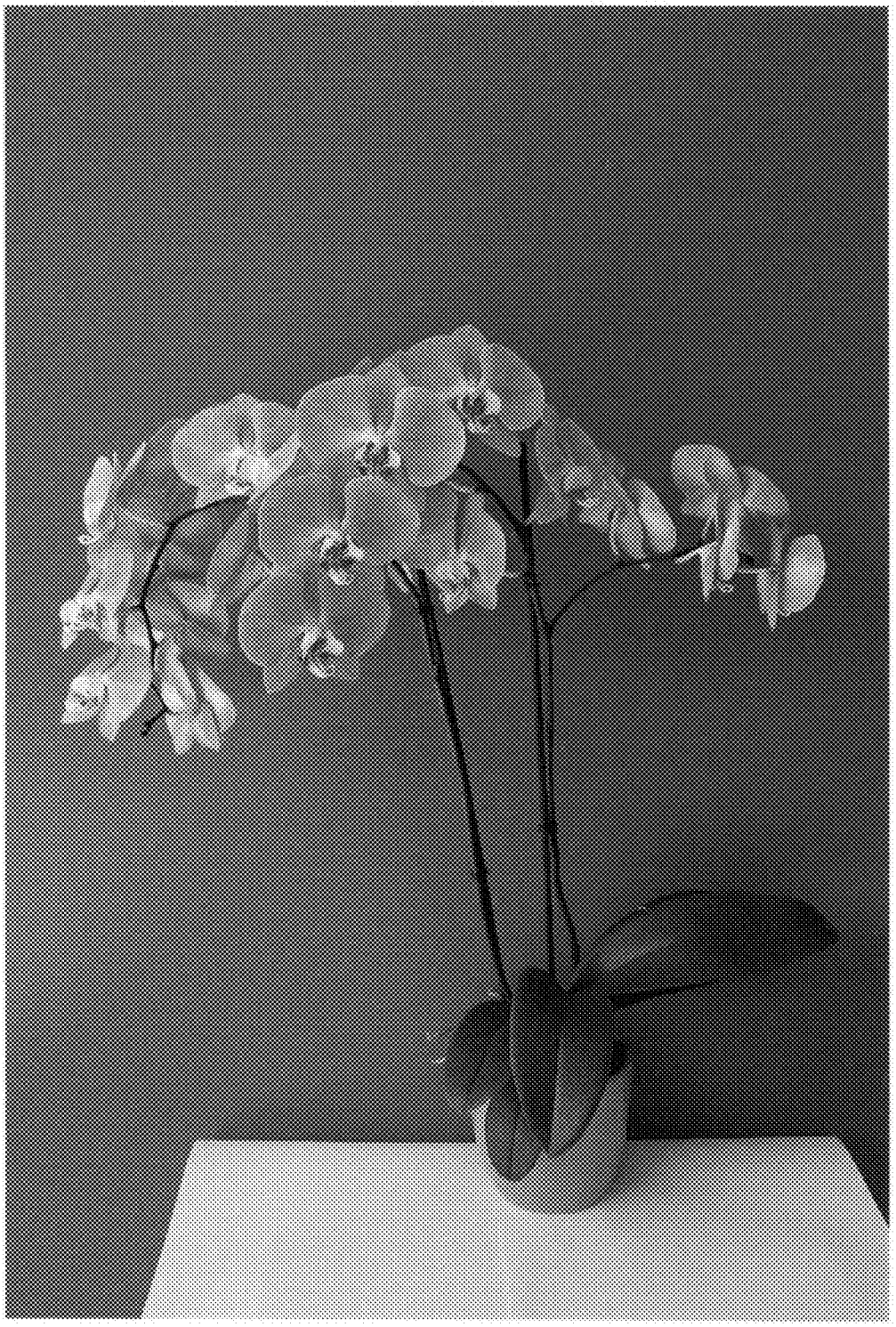

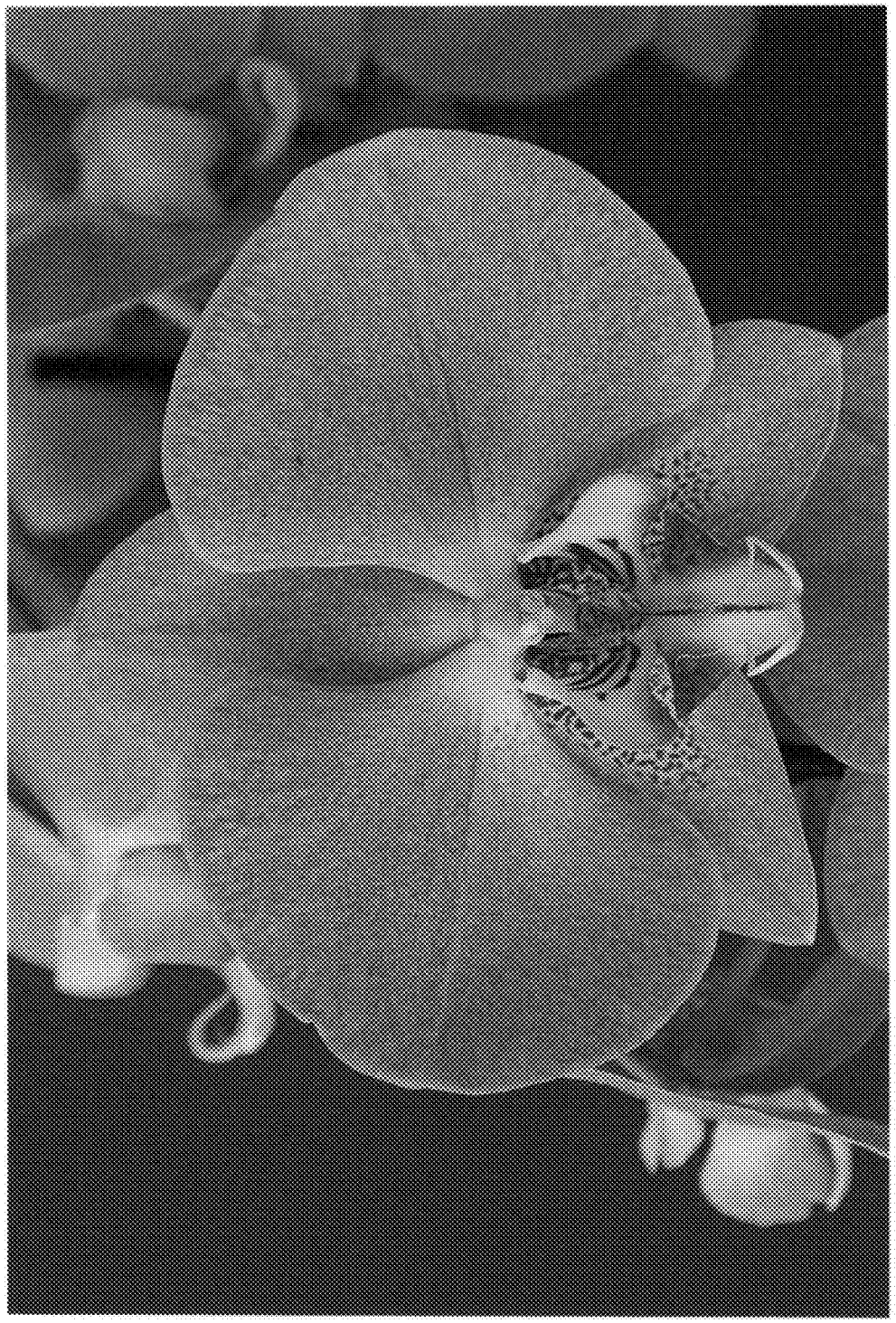

* * * * *